(12) United States Patent
Pimenta et al.

(10) Patent No.: US 9,820,924 B2
(45) Date of Patent: Nov. 21, 2017

(54) LIQUID HAND SOAPS AND BODY WASHES

(71) Applicant: Colgate-Palmolive Company, New York, NY (US)

(72) Inventors: Paloma Pimenta, Staten Island, NY (US); Darrick Carlone, New Vernon, NJ (US); Emma Alvarado, Somerville, NJ (US); Subhash Harmalker, Someret, NJ (US); Marian N. Holerca, Someret, NJ (US); Evangelia S. Arvanitidou, Princeton, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 15/038,240

(22) PCT Filed: Nov. 22, 2013

(86) PCT No.: PCT/US2013/071386
§ 371 (c)(1),
(2) Date: May 20, 2016

(87) PCT Pub. No.: WO2015/076816
PCT Pub. Date: May 28, 2015

(65) Prior Publication Data
US 2016/0287499 A1    Oct. 6, 2016

(51) Int. Cl.
| | | |
|---|---|---|
| *C11D 1/29* | (2006.01) | |
| *C11D 1/722* | (2006.01) | |
| *C11D 1/90* | (2006.01) | |
| *C11D 3/32* | (2006.01) | |
| *A61K 8/39* | (2006.01) | |
| *A61K 8/42* | (2006.01) | |
| *A61K 8/44* | (2006.01) | |
| *A61K 8/45* | (2006.01) | |
| *A61K 8/46* | (2006.01) | |
| *A61K 8/86* | (2006.01) | |
| *A61Q 19/10* | (2006.01) | |
| *A61K 8/41* | (2006.01) | |
| *A61K 8/90* | (2006.01) | |
| *A61K 8/60* | (2006.01) | |
| *A61K 8/81* | (2006.01) | |

(52) U.S. Cl.
CPC ............... *A61K 8/42* (2013.01); *A61K 8/416* (2013.01); *A61K 8/442* (2013.01); *A61K 8/447* (2013.01); *A61K 8/45* (2013.01); *A61K 8/463* (2013.01); *A61K 8/608* (2013.01); *A61K 8/817* (2013.01); *A61K 8/86* (2013.01); *A61K 8/90* (2013.01); *A61Q 19/10* (2013.01); *A61K 2800/596* (2013.01)

(58) Field of Classification Search
CPC .. C11D 1/29; C11D 1/722; C11D 1/90; C11D 3/32; A61K 8/39; A61K 8/42; A61K 8/44; A61K 8/45; A61K 8/46; A61K 8/86; A61Q 19/10
See application file for complete search history.

(56) References Cited

U.S. PATENT DOCUMENTS

| | | |
|---|---|---|
| 5,880,083 A | 3/1999 | Beaujean et al. |
| 6,906,016 B1 | 6/2005 | Tsaur |
| 7,749,949 B2 | 7/2010 | Tuzi et al. |
| 2001/0051173 A1 | 12/2001 | Nabi et al. |
| 2002/0103092 A1 | 8/2002 | Tashjian et al. |
| 2006/0281652 A1* | 12/2006 | Keenan ................ A61K 8/0208 510/141 |

FOREIGN PATENT DOCUMENTS

RU    2331405    8/2008

OTHER PUBLICATIONS

Colgate Palmolive "Shower Gel", XP-002726976, CP Database accession No. 1965623, Jan. 2013, pp. 1-2.*
James-Smith, Monica A., "*Molecular interactions in surfactant solution: from micelles to microemulsions*", Dissertation presented to the graduate school of the University of Florida in partial fulfillment of the requirements for the degree of doctor of philosophy University of Florida, 2006, pp. 19, 61, 62, and 146.
Database GNPD [Online] Mintel, Apr. 2011, "Hand Liquid Soap", retrieved from CP Database accession No. 1530254.
Database GNPD [Online] Mintel. Jan. 31, 2013, "Shower Gel", XP002726976, retrieved from CP Database accession No. 1965623.
International Search Report and Written Opinion issued in International Application No. PCT/US2013/071386, dated Jul. 21, 2014.

* cited by examiner

Primary Examiner — Brian P Mruk

(57) ABSTRACT

The disclosure provides a liquid hand soap or body wash, comprising (i) a surfactant system comprising $C_{8-18}$ alkyl-ether sulfate, cocamidopropyl betaine (CAPB), and N-(2 hydroxyethyl) fatty acid amide; (ii) a polyethylene oxide-polypropylene oxide block copolymer; and (iii) one or more polyalkoxylated mono- or di-fatty acid esters or amides, the composition allowing reduced surfactant levels, while still having good rheological properties.

16 Claims, No Drawings

LIQUID HAND SOAPS AND BODY WASHES

BACKGROUND

Liquid personal cleansers, e.g., liquid hand soaps and body washes, require minimal levels of surfactant to provide good cleaning and dispensing properties. At the same time, consumers demand a low cost product. While reducing the surfactant level may be desirable from a cost perspective, reducing the surfactant levels may damage the cleaning efficacy and rheological properties of the product. There is a need for liquid personal cleansers that have acceptable cleaning and rheological properties and that also are inexpensive to manufacture.

BRIEF SUMMARY

A number of combinations of surfactants and rheological modifiers are assessed to deliver formulations for efficacy, rheological properties and ingredient cost. Surfactant cost is generally the major ingredient cost for liquid personal care products, so a conventional approach to lowering formulation cost would be simply to decrease the concentration of surfactants. Lowering the surfactant levels, however, greatly affects the dispensing profile. When the surfactant concentrations are reduced, more salt has to be added to the formulations in order to achieve a target viscosity that is acceptable to the consumer (around 4000 mPas). Addition of salt, however, leads to a product that is stringy and messy to dispense, and therefore undesirable to the consumer. To address this problem, we needed to identify and measure the physical parameters underlying this product "stringiness".

Rheology measurements are conducted and correlated to consumer study responses. One particular rheological parameter, the critical relaxation time, $t_M^*$, turned out to correlate well with liquid hand soap dispensing acceptability. The relaxation time relates to the length of the surfactant micelles in solution. The longer the micelles are, the messier the product is to dispense. Therefore, the shorter the relaxation time, the better the product performance during dispensing. Experiments to evaluate the effect of the rheology modifiers on the relaxation time result in identification of prototypes with a relaxation time value equal or lower than commercial liquid hand soaps. Particular combinations of surfactants and rheological modifiers are found to provide lower relaxation time at a similar viscosity range of 3000-5000 mPas, using a significantly lower surfactant level (and thus having a significantly lower cost of goods), compared to existing commercial products.

In one aspect, provided is Composition 1, a liquid hand soap or body wash, comprising
  a. a surfactant system comprising $C_{8-18}$ alkyl-ether sulfate (e.g. sodium lauryl ether sulfate (SLES)), cocamidopropyl betaine (CAPB), and N-(2-hydroxyethyl) fatty acid amide (e.g., cocamide monoethanolamine (CMEA));
  b. a polyethylene oxide-polypropylene oxide block copolymer (e.g. POLOXAMER™ 124 (PLURONIC™ L44) polyethylene oxide-polypropylene oxide block copolymer having the formula (EO)x(PO)y(EO)z with x=8-14 (average 11), z=8-14 (average 11) and y=16-26 (average 21), POLOXAMER™ L35, or POLOXAMER™ L31); and
  c. one or more polyalkoxylated mono- or di-fatty acid esters or amides, e.g., selected from ($C_2$-$C_4$)alkoxylated mono($C_2$-$C_3$)alkanol isostearamide (for example PPG-2 hydroxyethyl coco/isostearamide or PPG-2 hydroxyethyl cocamide), polyethoxylated glyceryl fatty acid esters (for example PEG-18 glyceryl oleate/cocoate and/or PEG-7 glyceryl cocoate), polyethoxylated esters of fatty acids and saccharides (for example PEG-120 methyl glucose dioleate), and combinations thereof.

For example, in various aspects the present invention encompasses:
  1.1 Composition 1, wherein the $C_{8-18}$ alkyl-ether sulfate is of formula $CH_3(CH_2)_m CH_2(OCH_2CH_2)_n OSO_3X$, wherein m is 6-16, e.g., 10, n is 1-6, e.g., 2, 3 or 4, and X is Na or K, for example sodium lauryl ether sulfates, e.g., sodium laureth-2 sulfate $(CH_3(CH_2)_{10}CH_2(OCH_2CH_2)_2OSO_3Na)$.
  1.2 Any foregoing composition wherein the N-(2-hydroxyethyl) fatty acid amide comprises cocamide monoethanolamine.
  1.3 Any foregoing composition which is free of alkylpolyglucoside, e.g. decyl glucoside.
  1.4 Any foregoing composition wherein the polyethylene oxide-polypropylene oxide block copolymer comprises polyethylene oxide-polypropylene oxide block copolymer having the formula (EO)x(PO)y(EO)z with x=8-14 (average 11), z=8-14 (average 11) and y=16-26 (average 21).
  1.5 Any foregoing composition wherein the one or more polyalkoxylated mono- or di-fatty acid esters or amides are selected from PPG-2 hydroxyethyl coco/isostearamide, PEG-18 glyceryl oleate/cocoate, PEG-7 glyceryl cocoate, PEG-120 methyl glucose dioleate, and combinations thereof.
  1.6 Any foregoing composition wherein the one or more polyalkoxylated mono- or di-fatty acid esters or amides comprise PEG-120 methyl glucose dioleate.
  1.7 Any foregoing composition wherein the surfactant system comprises sodium lauryl ether sulfate, cocamidopropyl betaine and cocamide monoethanolamine.
  1.8 Any foregoing composition wherein the surfactant system comprises sodium lauryl ether sulfate, cocamidopropyl betaine and cocamide monoethanolamine; the polyethylene oxide-polypropylene oxide block copolymer is (EO)x(PO)y(EO)z with x=8-14 (average 11), z=8-14 (average 11) and y=16-26 (average 21); and the one or more mono- or di-ester or amide derivatives of fatty acids and polyalkylene glycols are selected from PPG-2 hydroxyethyl coco/isostearamide, PEG-18 glyceryl oleatelcocoate, PEG-7 glyceryl cocoate, PEG-120 methyl glucose dioleate, and combinations thereof.
  1.9 Any foregoing composition further comprising a skin conditioner or moisturizer, for example a polyquaternium compound, e.g., a copolymer of acrylamide and diallyldimethylammonium chloride, e.g., polyquaternium-7.
  1.10 Any foregoing composition further comprising at least 70 weight % water, e.g., at least 80 weight % water, for example 80 to 90 weight % water.
  1.11 Any foregoing composition wherein the total amount of surfactant is 5 to 9 weight %, e.g., 8 to 9 weight %.
  1.12 Any foregoing composition wherein the amount of $C_{8-18}$ alkyl-ether sulfate is less than 7 weight %, e.g., 5.5 to 6.5 weight %, e.g., about 6 weight %.
  1.13 Any foregoing composition wherein the amount of cocamidopropyl betaine is less than 2.5 weight %, e.g., 1.5 to 2.4 weight %, e.g., about 2 weight %.
  1.14 Any foregoing composition wherein the amount of N-(2-hydroxyethyl) fatty acid amide is 0.2 to 0.5 weight %, e.g., about 0.4 weight %.

1.15 Any foregoing formulation, wherein the amount of polyethylene oxide-polypropylene oxide block copolymer is 0.01 to 0.15 weight %, e.g. 0.02 to 0.06 weight %, e.g., about 0.05 weight %.

1.16 Any foregoing formulation wherein the one or more polyalkoxylated mono- or di-fatty acid esters or amides comprises PEG-120 methyl glucose dioleate, e.g., in an amount of 0.01 to 0.1 weight %, e.g., about 0.04 weight %.

1.17 Any foregoing formulation wherein the one or more polyalkoxylated mono- or di-fatty acid esters or amides comprises PEG-18 glyceryl oleate/cocoate, e.g., in an amount of 0.01 to 0.1 weight %, e.g., about 0.2 weight %.

1.18 Any foregoing formulation wherein the one or more polyalkoxylated mono- or di-fatty acid esters or amides comprises PPG-2 hydroxyethyl coco/isostearamide, e.g., in an amount of 0.05 to 0.1 weight %.

1.19 Any foregoing composition further comprising an effective amount of preservative (e.g., selected from sodium salicylate, sodium benzoate, and combinations thereof), dye, fragrance, chelator (e.g., tetrasodium EDTA), viscosity-modifying salts (e.g., sodium chloride, sodium sulfate, and combinations thereof), and pH adjusting agents (e.g. citric acid).

1.20 Any foregoing composition further comprising an effective amount of an antibacterial agent, e.g., sodium salicylate and sodium benzoae.

1.21 Any foregoing composition, wherein the zero-shear viscosity is between about 3,000-4,000 mPas (e.g., 3,200-3,800 mPas).

1.22 Any foregoing composition wherein the micelle relaxation time is less than 0.06 seconds, e.g., 0.04 to 0.05 seconds.

1.23 Any foregoing composition which is cosmetically acceptable, e.g., as defined herein.

1.24 Any foregoing composition which is substantially clear.

1.25 Any foregoing composition which is a liquid hand soap.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The term "soap" as used herein is given a broad meaning, and is intended to encompass agents to clean the hands and/or the body, including cosmetic or detergent substances as described in 21 C.F.R. 701.20, particularly products generally referred to as liquid hand soaps and body washes. Applicants recognize that, in some particular contexts, the term "soap" may be given a narrow definition as being a product primarily composed of alkali salts of fatty acids, but the term as used herein is not intended to be so limited. Thus a liquid hand soap, for example, need not contain any alkali salts of fatty acids.

Unless otherwise specifically identified, the ingredients for use in the compositions of the present invention should be cosmetically acceptable ingredients. By "cosmetically acceptable" is meant suitable for use in a formulation for topical application to human skin. A cosmetically acceptable excipient, for example, is an excipient that is suitable for external application in the amounts and concentrations contemplated in the formulations of this invention, and includes for example excipients which are "Generally Recognized as Safe" (GRAS) by the United States Food and Drug Administration. Representative excipients include water, oils, both vegetable and mineral, soap bases, cream bases, lotion bases, ointment bases and the like, particularly aqueous detergent carriers, for example liquid hand soaps or body washes. In some embodiments, the cosmetically acceptable carrier contains topically acceptable quaternary ammonium compounds, which may serve as moisturizers or as antibacterial agents. They may additionally include buffers, preservatives, antioxidants, fragrances, emulsifiers, dyes and excipients known or used in the field of cosmetic formulation, including for example inert fillers, anti-irritants, tackifiers, excipients, fragrances, opacifiers, antioxidants, gelling agents, stabilizers, surfactant, emollients, coloring agents, preservatives, buffering agents, and other conventional components of topical formulations as are known in the art.

The compositions and formulations as provided herein are described and claimed with reference to their ingredients, as is usual in the art. As would be evident to one skilled in the art, the ingredients may in some instances react with one another, on that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Polyethylene oxide-polypropylene oxide block copolymer (poloxamers) for use in Compositions 1, et seq. are nonionic triblock copolymers composed of a central hydrophobic chain of polyoxypropylene (poly(propylene oxide)) flanked by two hydrophilic chains of polyoxyethylene (poly (ethytene oxide)), for example compounds known under the trade names Synperonic®, Pluronic® and Kolliphor®. By convention, these copolymers may be named as "poloxamer" (or "P") followed three digits, wherein the first two digits times 100 give the approximate molecular mass of the polyoxypropylene core in g/mol, and the last digit times 10 gives the approximate percentage polyoxyethylene content. Poloxamer 124 ((EO)x(PO)y(EO)z with x=8-14 (average 11), z=8-14 (average 11) and y=16-26 (average 21)) thus has a polyoxypropylene molecular mass of about 1200 g/mol and a polyoxyethylene content of about 40%. In certain embodiments, poloxamers for use in Compositions 1, et seq. are liquid at room temperature and have a polyoxypropylene molecular mass of about 800-1600 g/mol and a polyoxyethylene content of about 30-50. In some embodiments, the compositions comprise poloxamer 124, e.g., Pluronic® L-44, commercially available from BASF.

Compositions 1, et seq. may in some embodiments additionally comprise skin conditioners or moisturizers, for example polyquaternium compounds. Polyquaternium is a term for polymers having quaternary ammonium centers in the polymer, useful in personal care products, e.g., as set forth in the International Nomenclature for Cosmetic Ingredients. Different polyquaterniums are distinguished by number, wherein the number corresponds to a particular polymer type. In some particular embodiments, Compositions 1, et seq. comprise Polyquaternium-7, which is a copolymer of acrylamide and diallyldimethylammonium chloride.

Polyalkoxylated mono- or di-fatty acid esters or amides for use in Compositions 1, et seq. include a. $(C_2-C_4)$alkoxylated mono$(C_2-C_3)$alkanol fatty acid amides, e.g. as disclosed in U.S. Pat. No. 6,635,607, incorporated herein by reference, e.g. of formula $R_1$—CO—NH—$CH_2$—$CH_2$—O—$(CH_2$—$CH(R_2)$—$O)_n$—H, wherein $R_1$ is a $C_{8-18}$ linear or branched hydrocarbon (for example wherein $R_1$—CO— is an acyl from coconut oil fatty acids, isostearic acid, or mixtures thereof), $R_2$ is H, $CH_3$, $CH_2CH_3$, and n is 2 or 3; for example PPG-2 hydroxyethyl coco/isostearamide, (e.g., Promidium-2®, available from Croda);

b. polyethoxylated glyceryl fatty acid esters, for example PEG-18 glyceryl oleate/cocoate (e.g., Antil 171, available from Evonik-Goldschmidt), and PEG-7 glyceryl cocoate;

c. polyethoxylated esters of fatty acids and saccharides, e.g. PEG-120 methyl glucose dioleate (e.g. Glucamate® DOE-120, available from Lubrizol); and d. combinations of any of the foregoing.

In some embodiments, Compositions 1, et seq. may also comprise suitable antioxidants; that is, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-fert-butylphenol, erythorbic acid, gum guaiac, propyl gallate, thiodipropionic acid, dilauryl thiodipropionate, tert-butylhydroquinone and tocopherots such as vitamin E, and the like, including pharmaceutically acceptable salts and esters of these compounds; e.g., butylated hydroxytoluene, butylated hydroxyanisole, propyl gallate, ascorbic acid, pharmaceutically acceptable salts or esters thereof, or mixtures thereof; for example butylated hydroxytoluene. When the topical formulations of the present invention contain at least one antioxidant, the total amount of antioxidant present is from about 0.001 to 0.5 wt %, 0.05 to 0.5 wt %, e.g. about 0.1%.

Compositions 1, et seq. may also comprise suitable preservatives. Preservatives are compounds added to a formulation to act as an antimicrobial agent. Among preservatives known in the art as being effective and acceptable parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, sodium benzoate, sodium salicylate and various mixtures thereof. When the compositions contain at least one preservative, the total amount of preservative present is from about 0.01 to about 1 wt %, depending on the characteristics of the particular preservatives selected and the amount required for effective preservation in the particular formulation. In some embodiments, the compositions comprise sodium benzoate and sodium salicylate in a total amount of 0.1% to 1%.

Compositions 1, et seq., may in some embodiments also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-Amino-2-[(2-amino-5-methylphenoxy)methyl]-6-methoxyquinoline-N5N,N',N'-tetraacetic acid, tetrapotassium salt (QUIN-2). When the compositions contain at least one chelating agent, the total amount of chelating agent present is 0.005 to 2 weight % by weight, depending on the particular chelator and formulation selected. For example, in some embodiments, the compositions contain 0.05 to 0.3 weight %. e.g., about 0.01 weight % of tetrasodium EDTA.

Compositions 1, et seq. may also comprise suitable pH adjusting agents and/or buffers to adjust and maintain the pH of the formulation to a suitable range, e.g., pH 6-8 or approximately neutral pH, for example citric acid in amounts of 0.1 to 0.2 weight % to adjust the pH as required.

EXAMPLES

Zero Shear Viscosity is measured as follows.
Instrument: Stress controlled rheometer, TA Series AR2000.
Geometry: 4 cm 2 degree acrylic cone
Experiment: Frequency sweep @25° C. and 1% Strain from 0.1-100 rad/s
Calculations are made using the data generated from the frequency sweep to determine relaxation time and shear viscosity.

Example 1

Lowering the surfactant level while adjusting the salts to maintain viscosity is found to produce a product having significantly greater micelle relaxation times, e.g. greater than 0.1 sec, as seen in Table 1, and consequently, significantly greater stringiness, making the product messy and difficult to dispense. Different polymers are assessed for their effects on micelle relaxation time ($t_M$) and viscosity.

TABLE 1

| Formula | Active Surfactant concentration (wt %) | Relaxation Time (s) | Zero Shear Viscosity [mPas] |
|---|---|---|---|
| Base Only (no additives) | 8.2 | 0.1369 | 5590 |
| 0.01% DOE 120 | 8.2 | 0.1665 | 7611 |
| 0.1% DOE 120 | 8.2 | 0.2688 | 18543 |
| 0.01% poloxamer 124 | 8.2 | 0.0617 | 2013 |
| 0.15% poloxamer 124 | 8.2 | 0.0189 | 254 |
| 0.05% Antil | 8.2 | 0.1293 | 5984 |
| 0.1% Antil | 8.2 | 0.1194 | 6137 |
| 0.05% Promidium | 8.2 | 0.1636 | 7752 |
| 0.1% Promidium | 8.2 | 0.1667 | 8158 |

While none of the rheology modifiers individually are effective to address the problem of reducing stringiness while maintaining viscosity, particular combinations are found to provide good rheological properties, as seen below.

Example 2—Formulations

Formulations are prepared using various levels and types of surfactants and rheology modifiers. Formulations having good rheological profiles and reduced surfactant (AI) levels are identified, e.g., as set forth on Table 2:

TABLE 2

| Surfactant | Commercial formulation (active wt %) | Prototype 1a (active wt %) | Prototype 2 (active wt %) |
|---|---|---|---|
| Sodium laureth/pareth | 7 | 5.9 | 5.6 |
| CAP betaine | 2.6 | 1.8 | 2.5 |
| CMEA | — | 0.37 | 0.37 |
| Decyl Glucoside | 1 | — | — |
| Total surfactant | 10.6 | 8.1 | 8.5 |

Ingredients of these formulations are as set forth below.
Prototype 1a:

| Wt (%) Active | Ingredient |
|---|---|
| Q.S. | Di Water and minors (fragrance, color, preservatives) |
| 5.9 | SLES |
| 1.8 | CAP Betaine |
| 0.1 | Polyquaternium 7 |
| 0.73 | Sodium Chloride |
| 0.37 | CMEA |
| 0.04 | PEG-18 glyceryl oleate/cocoate |
| 0.02 | Pluronic L-44 |
| 0.01 | PEG-7 Glyceryl Cocoate |

Prototype 1b:

| Wt % Active | Ingredient |
|---|---|
| Q.S. | DI Water and minors (fragrance, color, preservatives) |
| 5.8 | SLES |
| 1.8 | CAP Betaine |
| 0.1 | Polyquaternium 7 |
| 1 | Sodium Chloride |
| 0.37 | CMEA |
| 0.05 | Pluronic L-44 |
| 0.01 | PEG-7 Glyceryl Cocoate |

Prototype 2

| Wt % Active | Ingredient |
|---|---|
| Q.S. | DI Water and minors (fragrance, color, preservatives) |
| 5.5 | SLES |
| 2.5 | CAP Betaine |
| 0.1 | Polyquaternium 7 |
| 1 | Sodium Chloride |
| 0.37 | CMEA |
| 0.05 | Pluronic L-44 |
| 0.04 | PEG-120 Dioleate |
| 0.01 | PEG-7 Glyceryl Cocoate |

The table below (Table 3) demonstrates the micelle relaxation times and shear viscosity for the two commercial liquid hand soap formulations and Prototypes 1a, 1b, and 2. As noted above, lowering the surfactant level while adjusting the salts to maintain viscosity led to a product having significantly greater micelle relation times, and consequently, significantly greater stringiness, making the product messy and difficult to dispense. In the particular formulations of this Example, however, while the weight percent of the surfactant is lower in the formulations of this Example, the relaxation times are lowered. Accordingly, the liquid hand soaps of this Example are an improvement over the market formulations, given that they can be produced with less surfactant, have a decreased micelle relaxation time and so are more cleanly dispensed, but still have a comparable shear viscosity to what is currently on the market.

TABLE 3

| Formula Type | Relaxation Time (s) | Zero Shear Viscosity (mPas) |
|---|---|---|
| Market Formulation 1 | 0.0615 | 4797 |
| Market Formulation 2 | 0.0603 | 4274 |
| Prototype 1B | 0.0488 | 3231 |
| Prototype 1A | 0.0512 | 3820 |
| Prototype 2 | 0.0444 | 3583 |

What is claimed is:

1. A composition that is a liquid hand soap or liquid body wash, comprising:
   a surfactant system comprising $C_{8-18}$ alkyl-ether sulfate, cocamidopropyl betaine, and N-(2-hydroxyethyl) fatty acid amide;
   a polyethylene oxide-polypropylene oxide block copolymer; and
   one or more polyalkoxylated mono- or di-fatty acid esters or amides,
   wherein the $C_{8-18}$ alkyl-ether sulfate is present in an amount of from about 5.5 to about 6.5 weight % based on a total weight of the composition,
   wherein the cocamidopropyl betaine is present in an amount of from about 1.5 to about 2.4 weight % based on a total weight of the composition,
   wherein the N-(2-hydroxyethyl) fatty acid amide is present in an amount of from about 0.2 to about 0.5 weight % based on a total weight of the composition, and
   wherein the composition has a zero-shear viscosity of from about 3,000 to about 4,000 mPas.

2. The composition of claim 1, wherein the $C_{8-18}$ alkyl-ether sulfate comprises a compound of formula $CH_3(CH_2)_m CH_2(OCH_2CH_2)_n OSO_3X$, wherein m is 6-16; n is 1-6; and X is Na or K.

3. The composition of claim 1, wherein the N-(2-hydroxyethyl) fatty acid amide comprises cocamide monoethanolamine.

4. The composition of claim 1, wherein the polyethylene oxide-polypropylene oxide block copolymer has a formula $(EO)x(PO)y(EO)z$ with x=8-14, z=8-14 and y=16-26.

5. The composition of claim 1, wherein the one or more polyalkoxylated mono- or di-fatty acid esters or amides are selected from the group consisting of $(C_2-C_4)$alkoxylated mono$(C_2-C_3)$alkanol isostearamide, polyethoxylated glyceryl fatty acid esters, polyethoxylated esters of fatty acids and saccharides, and combinations thereof.

6. The composition of claim 5, wherein the one or more polyalkoxylated mono- or di-fatty acid esters or amides are selected from the group consisting of PPG-2 hydroxyethyl coco/isostearamide, PEG-18 glyceryl oleate/cocoate, PEG-7 glyceryl cocoate, PEG-120 methyl glucose dioleate, and combinations thereof.

7. The composition of claim 6, wherein the one or more polyalkoxylated mono- or di-fatty acid esters or amides comprise PEG-120 methyl glucose dioleate.

8. The composition of claim 1, wherein the surfactant system comprises sodium lauryl ether sulfate, cocamidopropyl betaine and cocamide monoethanolamine.

9. The composition of claim 1, wherein:
the surfactant system comprises sodium lauryl ether sulfate, cocamidopropyl betaine and cocamide monoethanolamine;
the polyethylene oxide-polypropylene oxide block copolymer is (EO)x(PO)y(EO)z with x=8-14, z=8-14 and y=16-26; and
the one or more polyalkoxylated mono- or di-fatty acid esters or amides are selected from the group consisting of PPG-2 hydroxyethyl coco/isostearamide, PEG-18 glyceryl oleate/cocoate, PEG-7 glyceryl cocoate, PEG-120 methyl glucose dioleate, and combinations thereof.

10. The composition of claim 1, further comprising a polyquaternium compound.

11. The composition of claim 1, further comprising at least 70 weight % water.

12. The composition of claim 1, wherein the total amount of surfactant is 5 to 9 weight %.

13. The composition of claim 1, wherein the amount of the polyethylene oxide-polypropylene oxide block copolymer is 0.01 to 0.15 weight %.

14. The composition of claim 1, wherein the composition does not include an alkylpolyglucoside surfactant.

15. The composition of claim 1, wherein the micelle relaxation time of the composition is less than 0.06 seconds.

16. The composition of claim 1, wherein the composition is a clear liquid hand soap.

* * * * *